United States Patent
Gao et al.

(10) Patent No.: US 9,321,705 B2
(45) Date of Patent: Apr. 26, 2016

(54) PROCESS FOR PRODUCING CUMENE

(75) Inventors: Huanxin Gao, Shanghai (CN); Bin Zhou, Shanghai (CN); Yilun Wei, Shanghai (CN); Ruifang Gu, Shanghai (CN); Hua Fang, Shanghai (CN); Shufang Ji, Shanghai (CN); Hui Yao, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 215 days.

(21) Appl. No.: 13/886,000

(22) PCT Filed: Nov. 15, 2011

(86) PCT No.: PCT/CN2011/001911
§ 371 (c)(1),
(2), (4) Date: May 16, 2013

(87) PCT Pub. No.: WO2012/065365
PCT Pub. Date: May 24, 2012

(65) Prior Publication Data
US 2013/0237730 A1 Sep. 12, 2013

(30) Foreign Application Priority Data

Nov. 17, 2010 (CN) .......................... 2010 1 0551951
Nov. 17, 2010 (CN) .......................... 2010 1 0551962

(51) Int. Cl.
*C07C 2/00* (2006.01)
*C07C 6/06* (2006.01)
*C07C 6/12* (2006.01)

(52) U.S. Cl.
CPC . *C07C 6/06* (2013.01); *C07C 6/126* (2013.01); *C07C 2529/08* (2013.01); *C07C 2529/70* (2013.01)

(58) Field of Classification Search
CPC ................ C07C 2/00; C07C 2/66; C07C 6/06
USPC ............................................ 585/400 S, 800 S
See application file for complete search history.

(56) References Cited

U.S. PATENT DOCUMENTS

| 2,382,318 A | 8/1945 | Ipatieff et al. |
| 4,954,325 A | 9/1990 | Rubin et al. |

(Continued)

FOREIGN PATENT DOCUMENTS

| CN | 1037699 A | 12/1989 |
| CN | 1058011 A | 1/1992 |

(Continued)

OTHER PUBLICATIONS

Cui Xiao-Ming, "Production Progress and Market Analysis of Cumene at Home and Abroad", CEH Marketing Research Report, 2006, vol. pp. 27-33,Chemical Techno-Economics, Research Institute of Beijing Yanshan Petrochemical Corp., Sinopec, Beijing 102550, China.

(Continued)

*Primary Examiner* — In Suk Bullock
*Assistant Examiner* — Sharon Pregler
(74) *Attorney, Agent, or Firm* — Buchanan Ingersoll & Rooney PC

(57) ABSTRACT

A process of producing isopropyl benzene which solves the problem of high amount of n-propyl benzene according to the prior art. The process separates the polyisopropyl benzene through a suitable rectification into two streams of relatively lighter and heavier components, wherein the content of diisopropylbenzene in the stream of relatively lighter components is controlled to be at least greater than 95 wt %, and the content of tri-isopropyl benzene in the stream of relatively heavier components is controlled to be at least greater than 0.5 wt %. Such a technical solution subjecting the two streams respectively to the transalkylation solves the problem raised from the prior art, and is useful for the industrial production of isopropyl benzene.

11 Claims, 1 Drawing Sheet

(56) References Cited

U.S. PATENT DOCUMENTS

| | | | |
|---|---|---|---|
| 4,992,606 A | | 2/1991 | Kushnerick et al. |
| 5,003,119 A | * | 3/1991 | Sardina et al. ............... 585/323 |
| 5,362,697 A | | 11/1994 | Fung et al. |
| 5,453,554 A | | 9/1995 | Cheng et al. |
| 5,522,984 A | | 6/1996 | Gajda et al. |
| 5,672,799 A | | 9/1997 | Perego et al. |
| 6,051,521 A | | 4/2000 | Cheng et al. |
| 6,162,416 A | | 12/2000 | Gajda et al. |
| 2010/0292519 A1 | * | 11/2010 | Bullen et al. ............... 585/304 |

FOREIGN PATENT DOCUMENTS

| | | |
|---|---|---|
| CN | 1751994 A | 3/2006 |
| CN | 200410066636.2 | 3/2006 |
| CN | 1915944 A | 2/2007 |
| CN | 101121523 A | 2/2008 |
| CN | 200610029979.0 | 2/2008 |
| CN | 101151230 A | 3/2008 |
| CN | 100491311 A | 5/2009 |
| WO | WO 91/18849 A1 | 12/1991 |

OTHER PUBLICATIONS

International Search Report (PCT/ISA/210) issued on Feb. 23, 2012, by the State Intellectual Property Office of the P.R. China as the International Searching Authority for International Application No. PCT/CN2011/001911.

Office Action issued on Jun. 5, 2013, by the State Intellectual Property Office of the People's Republic of China in corresponding Chinese Patent Application No. 201010551962.8. (7 pages).

Office Action issued on Feb. 14, 2014, by the State Intellectual Property Office of the People's Republic of China in corresponding Chinese Patent Application No. 201010551962.8. (6 pages).

Office Action issued on Aug. 22, 2014, by the State Intellectual Property Office of the People's Republic of China in corresponding Chinese Patent Application No. 201010551962.8. (7 pages).

* cited by examiner

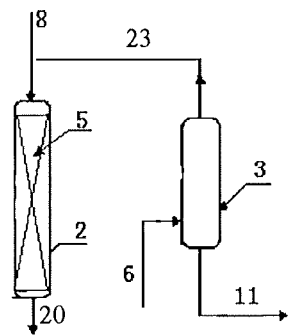
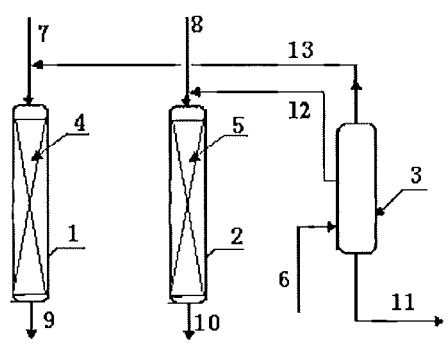
Fig. 1  Fig. 2
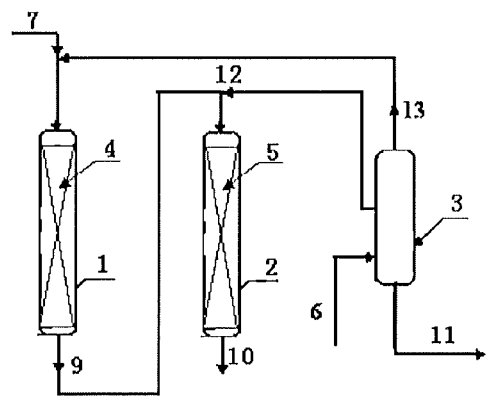
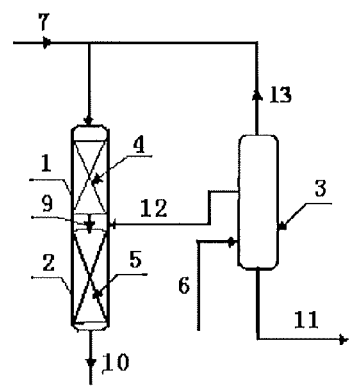
Fig. 3  Fig. 4

PROCESS FOR PRODUCING CUMENE

TECHNICAL FIELD

The present invention relates to a process for producing isopropyl benzene with benzene and propylene.

BACKGROUND

Isopropyl benzene is an important raw material for organic chemical industries, which is a main intermediate compound of producing phenol, acetone and alpha-methyl styrene. In industry, isopropyl benzene is prepared by alkylation of benzene with propylene, with a main by-product of polyisopropyl benzene. As early as 1945, UOP discloses a process for preparing isopropyl benzene by a reaction of propylene and benzene in the presence of a solid phosphoric acidic catalyst (SPA process) (U.S. Pat. No. 2,382,318). The SPA catalyst can't catalyze transalkylation of polyisopropyl benzene, thus, the SPA process can only be operated at a high molar ratio of benzene-to-olefin (5~7), and the yield of isopropyl benzene is only about 95%. In the 1980s, the Monsanto Company developed a process for producing isopropyl benzene using $AlCl_3$ as the alkylation catalyst, which had been practiced in industry. $AlCl_3$ cannot catalyze the transalkylation, thus the yield of isopropyl benzene of the $AlCl_3$ process for isopropyl benzene is still relatively low, while the problems of serious pollution and corrosion of the devices are present.

In the 1990s, the companies of Dow, CD Tech, Mobil-Badger, Enichem and UOP and so on (U.S. Pat. No. 4,992,606, U.S. Pat. No. 5,362,697, U.S. Pat. No. 5,453,554, U.S. Pat. No. 5,522,984, U.S. Pat. No. 5,672,799, U.S. Pat. No. 6,162,416, U.S. Pat. No. 6,051,521) disclose in succession fixed bed processes capable of conducting transalkylation with a microporous zeolite as the catalyst. In the present art, alkylation of benzene with propylene is carried out in an alkylation reactor. The polyisopropyl benzene generated from the alkylation process is separated by distillation system, mixed with benzene and then fed into an transalkylation reactor with a single catalyst bed for transalkylation.

In the transalkylation of polyisopropyl benzene with benzene, the molar ratio of benzene to polyisopropyl benzene, the space velocity of the raw materials, and the composition of the polyisopropyl benzene will affect significantly the conversion of the polyisopropyl benzene and the amount of the impurity of n-propyl benzene. Normally, the transalkylation of polyisopropyl benzene produces more amounts of the impurity of n-propyl benzene, which reduces the quality of the product isopropyl benzene significantly. Therefore, increasing the conversion of the polyisopropyl benzene and reducing the amount of n-propyl benzene generated from the transalkylation by optimizing the process is of significant importance for increasing the production efficiency and improving the quality of products.

SUMMARY OF THE INVENTION

The technical problem to be solved by the present invention is the relatively higher content of n-propyl benzene in transalkylation product, so as to provide a new process of producing isopropyl benzene. The process reduces significantly the content of n-propyl benzene and improves the product quality.

In order to solve the technical problem above, the present invention provides a technical solution as follows: a process of producing isopropyl benzene, comprising the steps of:

a) feeding a stream containing the polyisopropyl benzene into a polyisopropyl benzene column, resulting in a stream of relatively lighter components at the column top and a stream of relatively heavier components at the middle of the column through a separation by rectification; and b) allowing the stream of relatively lighter components and the stream of relatively heavier components into the first and second transalkylation zones respectively with a benzene stream, carrying out the transalkylation by contacting with a catalyst, and providing respectively a first and a second isopropyl benzene-containing streams, which are post-treated to provide a product isopropyl benzene.

Therein, the step b) can be carried out as follows, for example:

b1) feeding a first benzene stream and the stream of relatively lighter components into the first transalkylation zone from the top, contacting with the catalyst for an transalkylation, and providing a first isopropyl benzene-containing stream at the bottom; feeding a second benzene stream and the stream of relatively heavier components entering the second transalkylation zone from the top, contacting with the catalyst for an transalkylation, and providing a second isopropyl benzene-containing stream at the bottom of the second transalkylation zone; and feeding the first isopropyl benzene-containing stream and the second isopropyl benzene-containing stream respectively to the subsequent refining procedures, to provide a product isopropyl benzene; or b2) feeding a first benzene stream and the stream of relatively lighter components into the first transalkylation zone from the top, contacting with the catalyst for an transalkylation, and providing a first isopropyl benzene-containing stream at the bottom; feeding the first isopropyl benzene-containing stream and the stream of relatively heavier components together into the second transalkylation zone from the top, contacting with the catalyst for an transalkylation, and providing a second isopropyl benzene-containing stream at the bottom of the second transalkylation zone; and feeding the second isopropyl benzene-containing stream to the subsequent refining procedures, to provide a product isopropyl benzene.

It should be noted that the terms of "first", "second" and so on used in the process described above are provided for the only purpose of convenience of description and understanding, which distinguish the different subjects but never make any specific limitation to the time and/or spatial sequences/arrangements thereof.

In the above technical solution, in step b1), the weight ratio of the first benzene stream to the stream of relatively lighter components is in the range of 0.3-5, more preferably 0.7-3; and the weight ratio of the second benzene stream to the stream of relatively heavier components is in the range of 0.3-5, more preferably 0.7-3. In step b2), the weight ratio of the first benzene stream to the stream of relatively lighter components is in the range of 0.3-5, more preferably 0.7-3; the weight ratio of the first isopropyl benzene-containing stream to the stream of relatively heavier components is in the range of 0.3-5, more preferably 0.7-3; and the weight ratio of the first benzene stream to the stream containing the polyisopropyl benzene is in the range of 0.3-5. In the stream of relatively lighter components, the content of diisopropylbenzene is preferably in the range of 96-100 wt %. In the stream of relatively heavier components, the content of tri-isopropylbenzene is preferably in the range of 1-50 wt %.

In the technical solutions above, the first transalkylation zone and the second transalkylation zone can be each in the form of a fixed bed reactor, wherein the catalyst loaded is selected from the group consisting of Y zeolite, Beta zeolite, mordenite, SHY-1, SHY-2 and a mesoporous molecular sieve, such as MCM-22 introduced by U.S. Pat. No. 4,954, 325. The SHY-1 can be prepared according to the process disclosed by CN200410066636.2, and the SHY-2 can be prepared according to the process disclosed by CN200610029979.0.

In the technical solutions above, the reaction conditions of the first transalkylation zone can comprise, for example: a reaction temperature of 130~190 degrees C., a reaction pressure of 1.0-3.0 MPa, and a liquid space velocity of 0.5-10 hour$^{-1}$. The reaction conditions of the second transalkylation zone can comprise, for example: a reaction temperature of 150~210 degrees C., a reaction pressure of 1.0~3.0 MPa, and a liquid space velocity of 0.5-10 hour$^{-1}$. The operation conditions of the polyisopropyl benzene column can comprise, for example: an operation pressure of −300 to 0 kPa, a column top temperature of 120-160 degrees C., and a column bottom temperature of 190-250 degrees C.

In the process according to the present invention, the pressure means a gage pressure. The stream containing the polyisopropyl benzene means a product stream obtained after the alkylation conducted by benzene and propylene in an alkylation reactor, which comprises benzene, isopropyl benzene, diisopropylbenzene, tri-isopropyl benzene and n-propyl benzene. The polyisopropyl benzene represents diisopropylbenzene and tri-isopropyl benzene, which is generally present in the alkylation product stream in an amount of 90-100% by weight. The raw material of benzene can be fresh benzene, recycled benzene from the subsequent processing section(s) or a mixture thereof.

The process according to the present invention cuts the polyisopropyl benzene through a suitable rectification into two streams of relatively lighter and heavier components, wherein the content of diisopropylbenzene in the stream of relatively lighter components is controlled to be at least greater than 95 wt %, and the content of tri-isopropyl benzene in the stream of relatively heavier components is controlled to be at least greater than 0.5 wt %. These two streams are subjected respectively to the transalkylation, reducing the content of n-propyl benzene so significantly that the content of n-propyl benzene in the isopropyl benzene is as minimum as 320 ppm, thereby the product quality is increased and better technical effect is obtained.

DESCRIPTION OF DRAWINGS

FIG. 1 is a flow chart of a process according to the prior art.

FIGS. 2, 3 and 4 are flow charts of a process according to the present invention.

In FIG. 2, the first transalkylation zone and the second transalkylation zone are in the form of two separate fixed bed reactors in parallel.

In FIG. 3, the first transalkylation zone and the second transalkylation zone are in the form of two separate fixed bed reactors in series.

In FIG. 4, the first transalkylation zone and the second transalkylation zone are contained in one fixed bed reactor.

In FIGS. 1, 2, 3 and 4, 1 is the first transalkylation zone, 2 denotes the second transalkylation zone, 3 denotes the polyisopropyl benzene column, 4 denotes a catalyst bed layer of the first transalkylation zone, 5 denotes a catalyst bed layer of the second transalkylation zone, 6 denotes the stream containing the polyisopropyl benzene as a raw material, 7 denotes the first benzene stream as a raw material, 8 denotes the second benzene stream as a raw material, 9 denotes the first isopropyl benzene-containing stream as a discharge from the first transalkylation zone, 10 denotes the second isopropyl benzene-containing stream as a discharge from the second transalkylation zone, 11 denotes the stream of heavy components containing the tar as a bottom discharge from the polyisopropyl benzene column, 12 denotes the stream of relatively heavier components as a middle discharge from the polyisopropyl benzene column, 13 denotes the stream of relatively lighter components as a top discharge from the polyisopropyl benzene column, 20 denotes the isopropyl benzene-containing stream as a discharge from the transalkylation zone according to the prior art, 23 denotes a top discharge stream from the polyisopropyl benzene column according to the prior art.

EMBODIMENTS

FIG. 1 exemplifies a process according to the prior art, wherein a stream containing the polyisopropyl benzene 6 is fed into a polyisopropyl benzene column 3. After separation by rectification, a top discharge stream 14 from the polyisopropyl benzene column is obtained at the column top, and a stream of heavy components containing the tar 11 is obtained at the column bottom, which stream of heavy components containing the tar 11 is then fed into the subsequent procedure. A benzene stream 8 and the top discharge stream 14 from the polyisopropyl benzene column are fed into the transalkylation zone from the top thereof and contacted with the catalyst for an transalkylation, so as to provide a isopropyl benzene-containing stream 20 at the bottom.

The present invention provides a technical solution as follows: a process of producing isopropyl benzene, comprising the steps of:

a) feeding a stream containing the polyisopropyl benzene 6 into a polyisopropyl benzene column 3, resulting in a stream of relatively lighter components 13 at the column top, a stream of relatively heavier components 12 at the middle of the column and a stream of heavy components containing the tar 11 at the column bottom through a separation by rectification, in which the stream of heavy components containing the tar 11 is fed into the subsequent procedures; wherein the stream of relatively lighter components 13 contains at least greater than 95 wt % of diisopropylbenzene, and the stream of relatively heavier components 12 contains at least greater than 0.5 wt % of tri-isopropyl benzene, as showed by FIGS. 2, 3 and 4, for example; and b1) feeding a first benzene stream 7 and the stream of relatively lighter components 13 into the first transalkylation zone 1 from the top thereof, contacting with the catalyst for an transalkylation, and providing a first isopropyl benzene-containing stream 9 at the bottom; feeding a second benzene stream 8 and the stream of relatively lighter components 12 into the second transalkylation zone 2 from the top thereof, contacting with the catalyst for an transalkylation, and providing a second isopropyl benzene-containing stream 10 at the bottom; and feeding the first isopropyl benzene-containing stream 9 and the second isopropyl benzene-containing stream 10 respectively to the subsequent refining procedures, to provide a product isopropyl benzene, as showed by FIG. 2, for example; or b2) feeding a first benzene stream 7 and the stream of relatively lighter components 13 into the first transalkylation zone 1 from the top thereof, contacting with the catalyst for an transalkylation, and providing a first isopropyl benzene-containing stream 9 at the bottom; feeding the first isopropyl benzene-containing stream 9 and the stream of relatively lighter components 12 together into the second transalkylation zone 2 from the top thereof, contacting with the catalyst for an transalkylation, and providing a second isopropyl benzene-containing stream 10 at the bottom; and feeding the second isopropyl benzene-containing stream 10 to the subsequent refining procedures, to provide a product isopropyl benzene, as showed by FIGS. 3 and 4, for example.

Specifically, in FIG. 2, a stream containing the polyisopropyl benzene 6 is fed into a polyisopropyl benzene column 3. After separation by rectification, a stream of relatively lighter components 13 is obtained at the column top, a stream of relatively heavier components 12 is obtained at the column middle, and a stream of heavy components containing the tar 11 is obtained at the column bottom, which stream 11 is then fed into the subsequent procedures. The first benzene stream 7 and the stream of relatively lighter components 13 are fed into the first transalkylation zone 1 from the top and contacted with the catalyst for an transalkylation, so as to provide a first isopropyl benzene-containing stream 9 at the bottom. The second benzene stream 8 and the stream of relatively lighter components 12 are fed into the second transalkylation zone 2 from the top and contacted with the catalyst for an transalkylation, so as to provide a second isopropyl benzene-containing stream 10 at the bottom. The first isopropyl benzene-containing stream 9 and the second isopropyl benzene-containing stream 10 are fed into the subsequent refining procedures, to provide the product isopropyl benzene.

In FIGS. 3 and 4, a stream containing the polyisopropyl benzene 6 as a raw material is fed into a polyisopropyl benzene column 3. After separation by rectification, a stream of relatively lighter components 13 is obtained at the column top, a stream of relatively heavier components 12 is obtained at the column middle, and a stream of heavy components containing the tar 11 is obtained at the column bottom, which stream 11 is then fed into the subsequent procedure. The stuff benzene stream 7 and the stream of relatively lighter components 13 are fed into the first transalkylation zone 1 from the top and contacted with the catalyst for an transalkylation, so as to provide a first isopropyl benzene-containing stream 9 from the reaction. The first isopropyl benzene-containing stream 9 and the stream of relatively lighter components 12 are fed into the second transalkylation zone 2 from the top and contacted with the catalyst for an transalkylation, so as to provide a second isopropyl benzene-containing stream 10 from the reaction at the bottom. The stream 10 is fed into the subsequent refining procedures, to provide the product isopropyl benzene. During step b2), two separate columns can be used respectively as the first transalkylation zone 1 and the second transalkylation zone 2, as showed by FIG. 3. In addition, those skilled in the art can understand that, in one embodiment, one single column can be used to carry out the step b2), namely using one single column to contain both the first transalkylation zone 1 and the second transalkylation zone 2, as showed by FIG. 4.

The process according to the present invention cuts the polyisopropyl benzene through a suitable rectification into two streams of relatively lighter and heavier components, wherein the content of diisopropylbenzene in the stream of relatively lighter components 13 is controlled to be at least greater than 95 wt %, and the content of tri-isopropyl benzene in the stream of relatively heavier components 12 is controlled to be at least greater than 0.5 wt %. The distribution of the components in the polyisopropyl benzene column 3 is monitored, allowing the position at which the stream of relatively heavier components 12 is taken out from the column middle capable of being such that ensure the content of diisopropylbenzene in the stream of relatively lighter components of at least greater than 95 wt % and/or the content of tri-isopropyl benzene in the stream of relatively heavier components 12 of at least greater than 0.5 wt %.

The present invention will be further illustrated by the following examples.

EXAMPLE

Example 1

According to the procedures of FIG. 2, the first transalkylation reactor was loaded with 20 g of a catalyst of Beta zeolite, and the second transalkylation reactor was loaded with 50 g of a catalyst of MCM-22 zeolite. The reaction conditions of the first transalkylation reactor comprised: a reaction temperature of 150 degrees C., a reaction pressure of 1.2 MPa, a flow rate of the first benzene stream (stream 7) of 40 g/hr, a feeding rate of the polyisopropyl benzene (stream 13) of 20 g/hr, and a content of diisopropylbenzene in stream 13 of 98%. The reaction conditions of the second transalkylation reactor comprised: a reaction temperature of 180 degrees C., a reaction pressure of 1.5 MPa, a flow rate of the second benzene stream (stream 8) of 80 g/hr, a flow rate of the polyisopropyl benzene (stream 12) of 80 g/hr, and a content of tri-isopropylbenzene in stream 12 of 10%. The reaction was carried out continuously for 5 days.

The operation conditions of the polyisopropyl benzene column comprised: a column top temperature of 132 degrees C., a column bottom temperature of 215 degrees C., and an operation pressure of –80 MPa.

Reaction results: a conversion of the poly-isopropyl benzene of 65% and a content of n-propyl benzene in the isopropyl benzene of 450 ppm for the first transalkylation reactor; and a conversion of the poly-isopropyl benzene of 55% and a content of n-propyl benzene in the isopropyl benzene of 520 ppm for the second transalkylation reactor.

Example 2

According to the procedures of FIG. 2, the first transalkylation reactor was loaded with 30 g of a catalyst of Beta zeolite, and the second transalkylation reactor was loaded with 40 g of a catalyst of MCM-22 zeolite. The reaction conditions of the first transalkylation reactor comprised: a reaction temperature of 143 degrees C., a reaction pressure of 1.2 MPa, a flow rate of the first benzene stream (stream 7) of 60 g/hr, a feeding rate of the polyisopropyl benzene (stream 13) of 20 g/hr, and a content of diisopropylbenzene in stream 13 of 99%. The reaction conditions of the second transalkylation reactor comprised: a reaction temperature of 175 degrees C., a reaction pressure of 1.5 MPa, a flow rate of the second benzene stream (stream 8) of 60 g/hr, a flow rate of the polyisopropyl benzene (stream 12) of 40 g/hr, and a content of tri-isopropylbenzene in stream 12 of 8%. The reaction was carried out continuously for 5 days.

The operation conditions of the polyisopropyl benzene column comprised: a column top temperature of 128 degrees C., a column bottom temperature of 209 degrees C., and an operation pressure of –135 MPa.

Reaction results: a conversion of the poly-isopropyl benzene of 48% and a content of n-propyl benzene in the isopropyl benzene of 320 ppm for the first transalkylation reactor; and a conversion of the poly-isopropyl benzene of 55% and a content of n-propyl benzene in the isopropyl benzene of 430 ppm for the second transalkylation reactor.

Example 3

According to the procedures of FIG. 2, the first transalkylation reactor was loaded with 50 g of a catalyst of Beta zeolite, and the second transalkylation reactor was loaded with 40 g of a catalyst of SHY-1 zeolite. The reaction conditions of the first transalkylation reactor comprised: a reaction temperature of 150 degrees C., a reaction pressure of 1.2 MPa, a flow rate of the first benzene stream (stream 7) of 100 g/hr, a feeding rate of the polyisopropyl benzene (stream 13) of 60 g/hr, and a content of diisopropylbenzene in stream 13 of 98%. The reaction conditions of the second transalkylation reactor comprised: a reaction temperature of 180 degrees C., a reaction pressure of 1.5 MPa, a flow rate of the second benzene stream (stream 8) of 80 g/hr, a flow rate of the polyisopropyl benzene (stream 12) of 80 g/hr, and a content of tri-isopropylbenzene in stream 12 of 5%. The reaction was carried out continuously for 5 days.

The operation conditions of the polyisopropyl benzene column comprised: a column top temperature of 132 degrees C., a column bottom temperature of 213 degrees C., and an operation pressure of −95 MPa.

Reaction results: a conversion of the poly-isopropyl benzene of 62% and a content of n-propyl benzene in the isopropyl benzene of 430 ppm, for the first transalkylation reactor; and a conversion of the poly-isopropyl benzene of 45% and a content of n-propyl benzene in the isopropyl benzene of 480 ppm, for the second transalkylation reactor.

Example 4

According to the procedures of FIG. 2, the first transalkylation reactor was loaded with 50 g of a catalyst of Beta zeolite, and the second transalkylation reactor was loaded with 50 g of a catalyst of SHY-1 zeolite. The reaction conditions of the first transalkylation reactor comprised: a reaction temperature of 145 degrees C., a reaction pressure of 1.3 MPa, a flow rate of the first benzene stream (stream 7) of 120 g/hr, a feeding rate of the polyisopropyl benzene (stream 13) of 90 g/hr, and a content of diisopropylbenzene in stream 13 of 99%. The reaction conditions of the second transalkylation reactor comprised: a reaction temperature of 178 degrees C., a reaction pressure of 1.5 MPa, a flow rate of the second benzene stream (stream 8) of 120 g/hr, a flow rate of the polyisopropyl benzene (stream 12) of 100 g/hr, and a content of tri-isopropylbenzene in stream 12 of 12%. The reaction was carried out continuously for 5 days.

The operation conditions of the polyisopropyl benzene column comprised: a column top temperature of 125 degrees C., a column bottom temperature of 215 degrees C., and an operation pressure of −80 MPa.

Reaction results: a conversion of the poly-isopropyl benzene of 45% and a content of n-propyl benzene in the isopropyl benzene of 410 ppm, for the first transalkylation reactor; and a conversion of the poly-isopropyl benzene of 50% and a content of n-propyl benzene in the isopropyl benzene of 480 ppm, for the second transalkylation reactor.

Example 5

According to the procedures of FIG. 3, the first transalkylation zone and the second transalkylation zone were in the form of two separate fixed bed reactors in series. The first transalkylation zone was loaded with 15 g of a catalyst of Beta zeolite, and the second transalkylation zone was loaded with 60 g of a catalyst of SHY-1 zeolite. The reaction conditions of the first transalkylation zone comprised: a reaction temperature of 150 degrees C., a flow rate of the benzene stream (stream 6) of 110 g/hr, a feeding rate of the polyisopropyl benzene (stream 8) of 20 g/hr, and a content of diisopropylbenzene in stream 8 of 99%. The reaction conditions of the second transalkylation zone comprised: a reaction temperature of 178 degrees C., a pressure at the outlet of the second reaction zone of 1.5 MPa, a flow rate of stream 9 of 90 g/hr, and a content of tri-isopropyl benzene in stream 9 of 6%. The reaction was carried out continuously for 5 days.

The operation conditions of the polyisopropyl benzene column comprised: a column top temperature of 134 degrees C., a column bottom temperature of 215 degrees C., and an operation pressure of −80 MPa.

Reaction results: a conversion of the poly-isopropyl benzene of 60% and a content of n-propyl benzene in the isopropyl benzene of 460 ppm, for the first transalkylation zone; and a conversion of the poly-isopropyl benzene of 53% and a content of n-propyl benzene in the isopropyl benzene of 480 ppm, for the second transalkylation zone.

Example 6

According to the procedures of FIG. 3, the first transalkylation zone and the second transalkylation zone were two separate fixed bed reactors in series. The first transalkylation zone was loaded with 50 g of a catalyst of Beta zeolite, and the second transalkylation zone was loaded with 30 g of a catalyst of SHY-2 zeolite. The reaction conditions of the first transalkylation zone comprised: a reaction temperature of 148 degrees C., a flow rate of the benzene stream (stream 6) of 100 g/hr, a feeding rate of the polyisopropyl benzene (stream 8) of 50 g/hr, and a content of diisopropylbenzene in stream 8 of 99%. The reaction conditions of the second transalkylation zone comprised: a reaction temperature of 185 degrees C., a pressure at the outlet of the second reaction zone of 1.5 MPa, a flow rate of the polyisopropyl benzene (stream 9) of 25 g/hr, and a content of tri-isopropyl benzene in stream 9 of 8%. The reaction was carried out continuously for 5 days.

The operation conditions of the polyisopropyl benzene column comprised: a column top temperature of 129 degrees C., a column bottom temperature of 210 degrees C., and an operation pressure of −120 MPa.

Reaction results: a conversion of the poly-isopropyl benzene of 53% and a content of n-propyl benzene in the isopropyl benzene of 430 ppm, for the first transalkylation zone; and a conversion of the poly-isopropyl benzene of 56% and a content of n-propyl benzene in the isopropyl benzene of 510 ppm, for the second transalkylation zone.

Example 7

According to the procedures of FIG. 3, the first transalkylation zone and the second transalkylation zone were two separate fixed bed reactors in series. The first transalkylation zone was loaded with 40 g of a catalyst of Beta zeolite, and the second transalkylation zone was loaded with 40 g of a catalyst of MCM-49 zeolite. The reaction conditions of the first transalkylation zone comprised: a reaction temperature of 151 degrees C., a flow rate of the benzene stream (stream 6) of 80 g/hr, a feeding rate of the polyisopropyl benzene (stream 8) of 40 g/hr, and a content of diisopropylbenzene in stream 8 of 98%. The reaction conditions of the second transalkylation zone comprised: a reaction temperature of 171 degrees C., a pressure at the outlet of the second reaction zone of 1.5 MPa, a flow rate of the polyisopropyl benzene (stream 9) of 50 g/hr, and a content of tri-isopropyl benzene in stream 9 of 5%. The reaction was carried out continuously for 5 days.

The operation conditions of the polyisopropyl benzene column comprised: a column top temperature of 134 degrees C., a column bottom temperature of 215 degrees C., and an operation pressure of −80 MPa.

Reaction results: a conversion of the poly-isopropyl benzene of 57% and a content of n-propyl benzene in the isopropyl benzene of 450 ppm, for the first transalkylation zone; and a conversion of the poly-isopropyl benzene of 52%, and a content of n-propyl benzene in the isopropyl benzene of 470 ppm, for the second transalkylation zone.

Example 8

According to the procedures of FIG. 4, the first transalkylation zone and the second transalkylation zone were contained in one fixed bed reactor. The first transalkylation zone was loaded with 60 g of a catalyst of Beta zeolite, and the second transalkylation zone was loaded with 20 g of a catalyst of MCM-22 zeolite. The reaction conditions of the first transalkylation zone comprised: a reaction temperature of 145 degrees C., a flow rate of the benzene stream (stream 6) of 120 g/hr, a feeding rate of the polyisopropyl benzene (stream 8) of 70 g/hr, and a content of diisopropylbenzene in stream 8 of 99%. The reaction conditions of the second transalkylation zone comprised: a reaction temperature of 170 degrees C., a pressure at the outlet of the reactor of 1.5 MPa, a flow rate of the polyisopropyl benzene (stream 9) of 20 g/hr, and a content of tri-isopropyl benzene in stream 9 of 10%. The reaction was carried out continuously for 5 days.

The operation conditions of the polyisopropyl benzene column comprised: a column top temperature of 125 degrees C., a column bottom temperature of 208 degrees C., and an operation pressure of −150 MPa.

Reaction results: a conversion of the poly-isopropyl benzene of 53% and a content of n-propyl benzene in the isopropyl benzene of 300 ppm, for the first transalkylation zone; and a conversion of the poly-isopropyl benzene of 45% and a content of n-propyl benzene in the isopropyl benzene of 360 ppm, for the second transalkylation zone.

Comparative Example 1

According to the procedures of FIG. 1, the transalkylation unit had only one reactor, wherein a stream was drawn out from only the top of the polyisopropyl benzene column, which stream was fed entirely into the transalkylation reactor. The transalkylation zone was loaded with 50 g of a catalyst of Beta zeolite, a reaction temperature of 153 degrees C., a reaction pressure of 1.1 MPa, a flow rate of benzene of 100 g/hr, a flow rate of the polyisopropyl benzene of 80 g/hr, and a content of diisopropylbenzene in the polyisopropyl benzene of 96%. The reaction was carried out continuously for 5 days.

Reaction results: a conversion of the poly-isopropyl benzene of only 35%, and a content of n-propyl benzene in the isopropyl benzene of 560 ppm.

Comparative Example 2

It was same as the [comparative example 1], except for the transalkylation zone being loaded with 60 g of a catalyst of MCM-22 zeolite, a reaction temperature of 185 degrees C., a reaction pressure of 1.5 MPa, a flow rate of benzene of 80 g/hr, a flow rate of the polyisopropyl benzene of 80 g/hr, and a content of diisopropylbenzene in the polyisopropyl benzene of 96%. The reaction was carried out continuously for 5 days.

Reaction results: a conversion of the poly-isopropyl benzene of 55%, and a content of n-propyl benzene in the isopropyl benzene of 820 ppm.

Comparative Example 3

It was same as the [comparative example 1], except for the transalkylation zone being loaded with 60 g of a catalyst of MCM-22 zeolite, a reaction temperature of 172 degrees C., a reaction pressure of 1.5 MPa, a flow rate of benzene of 100 g/hr, a flow rate of the polyisopropyl benzene of 80 g/hr, and a content of diisopropylbenzene in the polyisopropyl benzene of 96%. The reaction was carried out continuously for 5 days.

Reaction results: a conversion of the poly-isopropyl benzene of 40%, and a content of n-propyl benzene in the isopropyl benzene of 630 ppm.

The invention claimed is:

1. A process of producing isopropyl benzene, comprising steps of:
   a) feeding a stream containing polyisopropyl benzene into a polyisopropyl benzene column, resulting in a stream of relatively lighter components at the top of the column, a stream of relatively heavier components at the middle of the column and a stream of heavy components containing tar at the bottom of the column through a separation by rectification, in which the stream of heavy components containing the tar is fed into subsequent procedures; wherein the stream of relatively lighter components contains at least greater than 95 wt % of diisopropylbenzene and the stream of relatively heavier components contains at least greater than 0.5 wt % of triisopropyl benzene; and
   b1) feeding a first benzene stream and the stream of relatively lighter components into a first transalkylation zone, contacting with a catalyst for transalkylation, and providing a first isopropyl benzene-containing stream at the bottom of the first transalkylation zone;
   feeding a second benzene stream and the stream of relatively heavier components into a second transalkylation zone, contacting with a catalyst for transalkylation, and providing a second isopropyl benzene-containing stream at the bottom of the second transalkylation zone; and
   feeding the first isopropyl benzene-containing stream and the second isopropyl benzene-containing stream into subsequent refining procedures, to provide a product isopropyl benzene; or
   b2) feeding a first benzene stream and the stream of relatively lighter components into a first transalkylation zone, contacting with a catalyst for transalkylation, and providing a first isopropyl benzene-containing stream at the bottom of the first transalkylation zone;
   feeding the first isopropyl benzene-containing stream and the stream of relatively heavier components into a second transalkylation zone, contacting with a catalyst for transalkylation, and providing a second isopropyl benzene-containing stream at the bottom of the second transalkylation zone; and
   feeding the second isopropyl benzene-containing stream into subsequent refining procedures, to provide a product isopropyl benzene.

2. The process of producing isopropyl benzene according to claim 1, wherein in step b1), a weight ratio of the first benzene stream to the stream of relatively lighter components is in a range of 0.3-5 and a weight ratio of the second benzene stream to the stream of relatively heavier components is in a range of 0.3-5; and in step b2), a weight ratio of the first benzene stream to the stream of relatively lighter components is in a range of 0.3-5 and a weight ratio of the first isopropyl benzene-containing stream to the stream of relatively heavier components is in a range of 0.3-5.

3. The process of producing isopropyl benzene according to claim 2, wherein in step b1), the weight ratio of the first benzene stream to the stream of relatively lighter components is in a range of 0.7-3 and the weight ratio of the second benzene stream to the stream of relatively heavier components is in a range of 0.7-3; and in step b2), the weight ratio of the first benzene stream to the stream of relatively lighter components is in a range of 0.7-3 and the weight ratio of the first isopropyl benzene-containing stream to the stream of relatively heavier components is in a range of 0.7-3.

4. The process of producing isopropyl benzene according to claim 1, wherein in the stream of relatively lighter components a content of diisopropylbenzene is in a range of 96-100 wt %; and in the stream of relatively heavier components a content of tri-isopropyl benzene is in a range of 1-50 wt %.

5. The process of producing isopropyl benzene according to claim 1, wherein the catalyst is selected from the group consisting of Y zeolite, Beta zeolite, mordenite, SHY-1, SHY-2 and MCM-22.

6. The process of producing isopropyl benzene according to claim 1, wherein in-the first transalkylation zone, a reaction temperature is in a range of 130~190 degrees C., a reaction pressure is in a range of 1.0~3.0 MPa, and a liquid weight space velocity is in a range of 0.5-10 $hour^{-1}$.

7. The process of producing isopropyl benzene according to claim 1, wherein in the second transalkylation zone, a reaction temperature is in a range of 150~210 degrees C., a reaction pressure is in a range of 1.0~3.0 MPa, and a liquid weight space velocity is in a range of 0.5-10 $hour^{-1}$.

8. The process of producing isopropyl benzene according to claim 1, wherein, for the polyisopropyl benzene column, an operation pressure is in a range of −300 to 0 kPa, a column top temperature is in a range of 120-160 degrees C., and a column bottom temperature is in a range of 190-250 degrees C.

9. The process of producing isopropyl benzene according to claim 1, wherein in step b2), a weight ratio of the first benzene stream to the stream containing the polyisopropyl benzene is in a range of 0.3-5.

10. The process of producing isopropyl benzene according to claim 1, wherein in the stream of relatively lighter components, a content of diisopropylbenzene is in a range of 98-100 wt %.

11. The process of producing isopropyl benzene according to claim 1, wherein in the stream of relatively heavier components, a content of tri-isopropyl benzene is in a range of 5-12 wt %.

* * * * *